United States Patent
Hagen et al.

(10) Patent No.: US 10,322,358 B2
(45) Date of Patent: Jun. 18, 2019

(54) DEVICE AND METHOD FOR SEPARATING A CYCLIC DIESTER FROM POLYMER MELTS

(71) Applicant: UHDE INVENTA-FISCHER GMBH, Berlin (DE)

(72) Inventors: Rainer Hagen, Berlin (DE); Udo Mühlbauer, Berlin (DE)

(73) Assignee: UHDE INVENTA-FISCHER GMBH, Berlin (DE)

(*) Notice: Subject to any disclaimer, the term of this patent is extended or adjusted under 35 U.S.C. 154(b) by 578 days.

(21) Appl. No.: 14/652,617

(22) PCT Filed: Oct. 17, 2013

(86) PCT No.: PCT/EP2013/071674
§ 371 (c)(1),
(2) Date: Jun. 16, 2015

(87) PCT Pub. No.: WO2014/095116
PCT Pub. Date: Jun. 26, 2014

(65) Prior Publication Data
US 2015/0329516 A1    Nov. 19, 2015

(30) Foreign Application Priority Data
Dec. 18, 2012 (EP) .................................. 12197885

(51) Int. Cl.
*B01D 7/02* (2006.01)
*C07D 319/12* (2006.01)
(Continued)

(52) U.S. Cl.
CPC .............. *B01D 7/02* (2013.01); *B01D 3/101* (2013.01); *B01D 3/105* (2013.01); *B01D 5/0003* (2013.01);
(Continued)

(58) Field of Classification Search
CPC ...... B01D 1/065; B01D 3/105; B01D 5/0003; B01D 7/02; B01D 19/0036
See application file for complete search history.

(56) References Cited

U.S. PATENT DOCUMENTS 5,023,350 A * 6/1991 Bhatia ................. C07D 319/12
                                                                549/274
5,770,682 A    6/1998 Ohara et al.
(Continued)

FOREIGN PATENT DOCUMENTS

| CN | 101591426 A | 12/2009 |
|----|-------------|---------|
| CN | 101820996 A | 9/2010  |

(Continued)

OTHER PUBLICATIONS

European Patent Office, International Search Report in International Application No. PCT/EP2013/071674 (dated Feb. 18, 2014).
(Continued)

*Primary Examiner* — Renee Robinson
(74) *Attorney, Agent, or Firm* — Leydig, Voit & Mayer, Ltd.

(57) ABSTRACT

The present invention relates to a device and also to a method for separating and recovering a cyclic diester, in particular dilactide or glycolide from polymer melts which include the cyclic diester as impurity. The device and also the method according to the invention allow recovery of the cyclic diester with a high yield and at the same time high purity.

13 Claims, 2 Drawing Sheets

(51) Int. Cl.
  *B01D 5/00* (2006.01)
  *B01D 3/10* (2006.01)
  *C08G 63/08* (2006.01)
  *C08G 63/78* (2006.01)
  *C08G 63/90* (2006.01)

(52) U.S. Cl.
  CPC ......... *B01D 5/0045* (2013.01); *C07D 319/12* (2013.01); *C08G 63/08* (2013.01); *C08G 63/785* (2013.01); *C08G 63/90* (2013.01)

(56) References Cited

U.S. PATENT DOCUMENTS

| | | | |
|---|---|---|---|
| 5,866,677 | A | 2/1999 | Maeda et al. |
| 6,875,839 | B2 | 4/2005 | Gerking et al. |
| 8,106,150 | B2 | 1/2012 | Oka et al. |
| 2009/0299018 | A1 | 12/2009 | Oka et al. |
| 2010/0261838 | A1 | 10/2010 | Hagen et al. |
| 2014/0316097 | A1 | 10/2014 | Hagen |
| 2015/0291733 | A1 | 10/2015 | Hess et al. |
| 2015/0329516 | A1 | 11/2015 | Hagen et al. |

FOREIGN PATENT DOCUMENTS

| | | |
|---|---|---|
| DE | 196 30 121 A1 | 1/1997 |
| EP | 0 499 747 A2 | 8/1992 |
| EP | 2 030 679 A1 | 3/2009 |
| EP | 2 055 730 A2 | 5/2009 |
| EP | 2 746 313 B1 | 8/2017 |
| TW | 2009/016186 A | 4/2009 |
| WO | WO 1998/036012 A1 | 8/1998 |
| WO | WO 2012/110117 A1 | 8/2012 |

OTHER PUBLICATIONS

European Patent Office, Written Opinion in International Application No. PCT/EP2013/071674 (dated Jun. 18, 2015).
European Patent Office, Notice Pursuant to Article 94(3) EPC in European Patent Application No. 12 197 885.2 (dated Jul. 13, 2015).
The Eurasian Patent Organization, Notification on the Necessity of Presenting Additional Materials in Eurasian Patent Application No. 201590365/28 (dated Nov. 3, 2016).
Intellectual Property Office Taiwan, Notice of Examination in Taiwanese Patent Application No. 102144317 (dated Feb. 3, 2017).
European Patent Office, Extended European Search Report in European Patent Application No. 12197885.2 (dated May 27, 2013).
The State Intellectual Property Office of People's Republic of China, First Office Action in Chinese Patent Application No. 201380062630.5 (dated Jun. 23, 2016).
Korean Intellectual Property Office, Notice of Preliminary Rejection in Korean Patent Application No. 10-2015-7008915 (dated Feb. 12, 2018).
Korean Intellectual Property Office, Notice of Preliminary Rejection in Korean Patent Application No. 10-2015-7008915 (dated Aug. 29, 2018).
Dorgan et al., "Fundamental solution and single-chain properties of polylactides," *J. Polym. Sci.: Part B: Polym. Physics*, 43: 3100-3111 (2005).
The State Intellectual Property Office of People's Republic of China, First Office Action in Chinese Patent Application No. 201710402721.9 (dated Nov. 23, 2018).
Instituto Mexicano De La Propiedad Industrial, First Office Action in Mexican Patent Application No. MX/a/2015/007606 (dated Nov. 22, 2018).

\* cited by examiner

DEVICE AND METHOD FOR SEPARATING A CYCLIC DIESTER FROM POLYMER MELTS

CROSS-REFERENCE TO RELATED APPLICATIONS

This patent application is the U.S. national phase of International Application No. PCT/EP2013/071674, filed on Oct. 17, 2013, which claims the benefit of European Patent Application No. 12197885.2, filed Dec. 18, 2012, the disclosures of which are incorporated herein by reference in their entireties for all purposes.

The present invention relates to a device and also to a method for separating and recovering a cyclic diester, in particular dilactide or glycolide from polymer melts which include the cyclic diester as impurity. The device and also the method according to the invention allow recovery of the cyclic diester with a high yield and at the same time high purity.

During polymerisation of PLA (polylactide), the polymer, because of the chemical ring-chain equilibrium, always comprises lactide in a concentration which is dependent upon the polymerisation temperature and is between approx. 1 and 5%. This value is independent of whether the PLA is produced by ring-opening polymerisation from lactide or by direct polycondensation from lactic acid. During ring-opening polymerisation, the concentration of the lactide can also assume higher values if the reaction is interrupted even before reaching the chemical equilibrium, e.g. by addition of a substance which deactivates the polymerisation catalyst.

Lactide concentrations in the PLA of more than 0.5% by weight make the polymer unusable for commercial purposes. During processing of PLA in the melt, such as spinning of threads, pouring of films, injection moulding etc, they lead to smoke which causes coughing, pollutes and corrodes devices. Lactide-containing PLA granulate absorbs moisture when stored in ambient air, lactide being hydrolysed to form the linear dimer of lactic acid. During processing from the melt, this hydrolysis product leads to the rapid decomposition of the PLA chains because of the high melting temperature required for this purpose of >170° C. (melting point of PLA), so that the polymer loses technically important properties, such as strength, transparency etc., and becomes unusable.

The lower the residual concentration of lactide in the PLA, the more durable are the products produced therefrom and the better it behaves during processing. For this reason, as low a concentration of lactide as possible is sought in the demonomerised PLA melt with an economically justifiable expenditure.

For these reasons, it is necessary to separate the lactide from the PLA after polymerisation up to a residual concentration below 0.5% by weight, preferably below 0.2% by weight. In the state of the art, this takes place by evaporation of the unconverted monomer from the melt. Vacuum or an inert carrier gas facilitate the evaporation, both frequently being used at the same time.

As is known, the separation of volatile components from a polymer melt takes place all the more completely the higher is the vacuum. On the other hand, a high vacuum makes deposition of the lactide from the vapour flow difficult. In the state of the art, the vacuum during the demonomerisation is therefore generally chosen such that a condensation in liquid form is possible. However, this limits the applicable vacuum to pressures which are significantly higher than the pressure at the triple point of the lactide. The lactide concentration achievable in the melt is hence likewise limited.

DE 196 30 121 A1 (Shimadzu) describes the monomer separation from PLA melt under vacuum with the help of a thin-film evaporator or horizontal single- or double-axle reactors. The separation of the monomer is effected by condensation in liquid form before it is returned to the polymerisation. The type of vacuum pump used is not described.

In EP 0 499 747 A2 (Novacor Chemicals), falling strand degasifiers, vent extruders or thin-film evaporators are proposed for the monomer separation. The vapours from the degassing are condensed in one or more condensers which are connected in succession. For the vacuum production, single- or multistage assemblies, not described in more detail, are used which produce a vacuum up to 0.002 atm. (=2 mbar). In order to reduce the partial pressure of the lactide to be separated and hence to facilitate the evaporation and to lower the residual monomer content in the polymer, the addition of carrier agents, such as nitrogen, toluene, ethylbenzene, are mentioned as a possibility. Although it is not mentioned explicitly, the use of the term "condenser" makes it obvious that the vapours are condensed in liquid form. Separation in solid form is not mentioned.

WO 98/36012 (Neste) prefers a falling strand degasifier for the vacuum evaporation, the polymer melt falling downwards in the form of threads in a container which is obviously not under vacuum. Hot inert gas, such as nitrogen or dry air, is blown into the degasifier in order to facilitate evaporation of the lactide from the surface of the falling threads. The lactide-containing hot gas is cooled rapidly to 20-40° C. after leaving the degasifier apparatus, lactide precipitating as crystalline powder. Preferably, this takes place in a "crystallisation chamber" by mixing with cold air. Without applying a vacuum, the pressure during the lactide separation is far above the triple point. A disadvantage of this method is the mixing of lactide with large quantities of inert gas which make it difficult to recover the lactide completely and which require additional complexity for separating the gas from the lactide powder (cyclone, gas filter).

In EP 2 055 730 A2 (Hitachi), the vapours from the PLA demonomerisation go into a container for recovery, which is evacuated with a vacuum pump. This container is cooled "with known means" so that lactide, e.g. in powder form, can be separated and reused as raw material for PLA production. No data relating to the technical design of the container and to the pressure- and temperature conditions during the separation are provided. Likewise, there are no data relating to the technical design of the vacuum pump. Removal of the powder from the container under vacuum is not resolved. Removal and transport of the powder for returning to the polymerisation process is difficult to implement because of the large specific surface of powder in the case of the known high sensitivity of the lactide relative to air humidity.

US 2009/0299018 A1 (Hitachi) describes a method and a device for vacuum production during PLA demonomerisation. The lactide vapour coming from the demonomerisation is condensed in a condenser in direct contact with a liquid which comprises lactic acid as main component. The liquid subsequently flows away into an atmospherically dipped collecting container and is returned from there to the condenser. A partial flow is removed from the collecting container in order to remove the condensed lactide from the circulation. In order to prevent blockage of the condenser by polycondensing lactide, aqueous lactic acid from the condensate of the subsequent vacuum step is supplied to the circulation.

The required vacuum is produced with a sequence of 3 jet pumps and a vacuum pump which is not described in more detail. Each of these jet pumps is equipped with an injection condenser which is connected to an atmospherically dipped condensate-collecting container. The condensate which consists mainly of water is guided in the circulation by going into a steam producer which provides the respective jet pump with operating steam. The method has the disadvantage that the condensed lactide occurs in a mixture with aqueous lactic acid. Because of the hydrolysis sensitivity thereof, it cannot be isolated from this mixture in pure form and therefore cannot be used directly as raw material of the ring-opening polymerisation. It reacts rapidly with water and lactic acid to form linear oligomers of lactic acid which, because of the too high end group content, are unusable for ring-opening polymerisation.

The presence of aqueous lactic acid during condensation of the lactide does not allow a pressure below the vapour pressure of the liquid mixture to be set. Hence the achievable vacuum is limited and consequently the residual concentration of lactide in the demonomerised PLA.

However, it is disadvantageous in all of the above-described methods that lactide from a demonomerisation unit cannot be recovered in such high purity for PLA that it makes it possible to return the lactide again directly to the polymerisation. It is known just as little from the state of the art to separate lactide in a solid, compact form, i.e. not as a powder, from the gas phase and to remove it from a container under vacuum. Furthermore, it is not known from the state of the art to undertake optimisation of the pressure ratios during such a demonomerisation which makes possible, at the same time, as high a yield as possible and, on the other hand, as high purity as possible of the recovered dilactide.

BRIEF SUMMARY OF THE INVENTION

It is the object of the invention, for reasons of economic efficiency, to recover the thus separated lactide in as pure a form as possible and with the greatest possible yield and to reuse it for the polymerisation. If the lactide is recovered in pure form, it is intended to be added directly to the raw material of the polymerisation in the case of ring-opening polymerisation. In the case of direct polycondensation of the lactic acid, this lactide is intended to be converted back into lactic acid by hydrolysis after the addition of water and added directly to the raw material for the polycondensation.

Volatile decomposition products of PLA which are produced in the polymerisation cause a problem which is thereby to be solved. They evaporate in the vacuum demonomerisation together with the lactide and should not condense, as far as possible, together with the latter. This can thereby concern lactic acid and the linear oligomers thereof, the main components of the thermal PLA decomposition, carbon monoxide, -dioxide, water and acetaldehyde, and also traces of higher aldehydes, such as propionaldehyde, butyraldehyde, crotonaldehyde and isovaleric aldehyde, in addition pentadiene, various furans, such as 2,5-dimethylfuran, carboxylic acids, particularly acetic acid and propionic acid in low concentrations. Further by-products can be produced from catalysts, stabilisers and other additives which are added before or after conclusion of the polymerisation. Some of these accompanying substances would contaminate the separated lactide by discolouring it, impairing the smell or chemically changing with ring opening. The lactide can then be returned as a raw material to the polymerisation only after a purification, such as recrystallisation or rectification. In the case of hydrolysis of the lactide, the produced lactic acid can be returned to the polycondensation only after purification.

This causes increased technical and economic expenditure. It is therefore a further object of the present invention to avoid such contamination of the separated lactide by by-products.

A further problem thereby to be solved is caused by the vacuum production for the demonomerisation. In the present invention, a high vacuum is required in order to achieve particularly low lactide concentrations in the demonomerised PLA and to separate the evaporated lactide in solid form. It is known to the person skilled in the art that, during condensation or desublimation, all the greater residual quantities of volatile components, such as lactide, remain in the gas flow because of the vapour pressure, the higher the vacuum is chosen. In addition, the inventors have made the discovery that it is extremely difficult to condense or to desublimate lactide vapours without small residual quantities, as solid or liquid aerosol together with the unavoidable leakage air, reaching the vacuum pumps and being deposited there. Even if these residual quantities are very small, they suffice, because of the corrosiveness and abrasiveness of the lactide, to destroy normal mechanical vacuum pumps (e.g. Roots-, rotary-slide valve-, screw pumps) within a short period of time. Therefore, a further object resided in finding vacuum assemblies which are not sensitive relative to lactide in solid or liquid form and not requiring expensive protective measures, such as being produced from corrosion- and abrasion-resistant materials.

An additional requirement of suitable vacuum pumps is scalability for large plant capacities, in particular avoidance of multistrand, parallel design. This would make the number of vacuum pumps rise proportionally to the plant capacity and therefore prevent the desired cost degression in the case of large plant capacities.

These objects are achieved by the features of the device and of the method described herein, and the advantageous developments thereof.

Within the scope of the description of the present invention, reference is made to the subsequent definitions which should be understood generally in a standard manner within the scope of the terminology used for describing the invention.

Desublimation: direct transition of a substance from the vaporous state into the solid state at pressures and temperatures below the triple point, i.e. without passing through the liquid state in between. The opposite of sublimation.

Separation device or lactide separator: there should be understood by that in the following a chemical engineering apparatus in which vaporous diester, e.g. lactide, can be separated in solid form on cooled surfaces and from which it can be recovered by melting at pressures and temperatures above the triple point.

Triple point: point in the pressure-temperature diagram of a pure substance in which all three phases, solid, liquid and vaporous, coexist. The phase boundary lines of solid/liquid, liquid/vapour and solid/vapour meet at the triple point. For pure L-lactide, this point is at 96.9° C. and 1.4 mbar. Within the scope of this invention, this value should be regarded merely as an example, it depends upon the composition of the separated lactide in the presented method. Both the content of lactide in the stereoisomers L-lactide, -lactide and D-lactide has an effect on the triple point, and by-products of PLA polymerisation which evaporate or sublimate together with the lactide in the demonomerisation. Here, lactic acid and other cyclic or linear oligomers of PLA should be mentioned and also decomposition products of the PLA polymerisation which were mentioned already in the description. Impurities in a pure substance such as L-lactide generally lower the melting point thereof. Because of the extensive pressure independence of the melting point, this also applies to the triple point. Impurities in the lactide accordingly shift the triple point in FIG. 2 to the left, on an imaginary extension of the vapour pressure curve a, to lower temperatures and pressures in comparison with pure L-lactide.

Degassing, degasifier: separation or apparatus for separating a volatile substance from a melt by evaporation or volatilisation, i.e. below the boiling point of the melt and above or below the boiling point of the pure volatile substance. Degassing and degasifier is used synonymously here with evaporation and evaporator.

Falling strand degasifier: continuous degasifier in which the polymer melt flow is divided by a large number of nozzle borings into strands (or also threads) which, in the vertical fall, pass through the interior of an evacuated container. In the falling time between exit of the melt from the boring and impinging on the container base any monomer contained evaporates. The melt is continuously withdrawn and discharged from the container base.

Atmospheric dipping: device known to the person skilled in the art for bringing and discharging liquid continuously from a system under vacuum to atmospheric pressure without a pump. In the case of water as liquid, the container under vacuum is disposed at more than 10 m height above a so-called dipping container (FIG. 1, no. 4 and 6) which contains water and is at atmospheric pressure. From the container under vacuum, a pipeline leads downwards into the dipping container where it ends below the water level. As a result of the vacuum, water in this pipe is suctioned upwards until the hydrostatic level of the water column balances out the pressure difference between the two containers. In the case of water, this level is at most 10 m above the level in the dipping container. Water can thus flow out of the vacuum at atmospheric pressure without being impeded. Liquids with a higher density than water, such as e.g. lactic acid, reach the goal already with a lower hydrostatic level.

According to the invention, a device is hence described for separating and recovering a cyclic diester of general Formula I

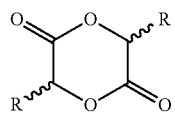

Formula 1

R being selected from hydrogen or linear or branched aliphatic radicals with 1 to 6 carbon atoms, from polymer melts, comprising the diester of general formula I, which comprises
 a) at least one demonomerisation device for removing the diester of general Formula I in gaseous aggregate state from the polymer melt,
 b) at least one separation device, which is connected subsequent to the at least one demonomerisation device and which is in connection with the at least one demonomerisation device in fluidic connection, e.g. via a pipeline, for separating the diester of general Formula I, in which the diester of general Formula I is converted via the solid or compact aggregate state into the liquid aggregate state, and also
 c) at least one device for producing a vacuum which is connected subsequent to the at least one separation device and which is in fluid connection with the at least one separation device.

The device according to the present invention hence comprises at least three essential components, namely a demonomerisation device, a separation device and also a device for producing a vacuum. The devices are thereby connected successively in series so that, by means of the low pressure produced by the device for producing the vacuum, gases or vapours can be conducted out of the demonomerisation device via the separation device. In the separation device, desublimation or separation of the diester of general Formula I is effected in the solid aggregate state on suitably cooled surfaces. Hence the separation temperature is not delimited at the bottom by the melting point of the lactide. Discharge of the thus separated diester from the separation device is effected however in the liquid aggregate state.

The device according to the invention enables efficient separation of the cyclic diester, i.e. a large part of the gaseously separated cyclic diester can be recovered in the separation device by the desublimation or separation in the solid aggregate state. In addition, it is likewise possible with the device according to the invention to recover the cyclic diester with high purity so that the cyclic diester is suitable for example immediately for further use, in particular for a ring-opening polymerisation.

A preferred embodiment provides that the at least one separation device has means with coolable and/or heatable surfaces, in particular pipes, pipe bundles, plates, plate registers and/or walls etc., on which the desublimation or separation of the diester of general Formula I is effected.

The at least one separation device, in particular the means with coolable or heatable surfaces of the separation device can be brought to the respective operating temperatures by active supply of corresponding cool or warm media. It is hereby advantageous if in front of the at least one separation device, at least one three-way valve is connected for supplying, in particular the means with coolable or heatable surfaces, with a cooling or heating medium and/or at least one three-way valve is connected subsequently for removing a cooling or heating medium. According to this embodiment, the respective separation device can hence be supplied optionally with a cooling or heating medium so that a corresponding alternating operation of the separation device is possible.

It is preferred in particular that the device according to the invention comprises at least two separation devices which can be operated alternately and are in fluidic connection via a three-way valve with the demonomerisation device and via a three-way valve with at least one device for producing a vacuum. This embodiment provides for example that, in the case of at least two separation devices, the one separation device is supplied with a cooling medium and hence is available for the separation of cyclic diester. The other deposition device can thereby be regenerated by for example supplying a heating medium to this separation device and the cyclic diester separated therein is thawed or melted and hence converted into the liquid aggregate state. The plurality of separation devices, in particular two separation devices, can thereby be connected respectively to the demonomerisation device via a common fluidic connection and respectively to the device for producing a vacuum so that for example the device in which precisely a separation of the cyclic diester is to be implemented is connectable, via the two sets of points, both to the demonomerisation device and to the device for producing the vacuum.

Advantageously, the at least one separation device has at least one base-side outlet, subsequent to which at least one collection tank for the diester of general Formula I is connected. Via the base-side outlet, during regeneration of the separation device, i.e. during heating and hence melting of the cyclic diester separated previously in solid aggregate state, the diester accumulated in the separation device can be discharged at the base-side and supplied to a collection tank.

The collection tank can serve for example for temporary storage of the dilactide, the possibility is likewise given that the collection tank is connected directly to a polymerisation device and the collected cyclic diester can be supplied to this polymerisation device via the collection tank.

Preferably, the at least one device for producing a vacuum is an ejector pump, in particular a steam ejector pump, or a cascade of at least two, preferably at least three, ejector pumps, in particular steam ejector pumps. In particular, the arrangement of a plurality of ejector pumps to form a cascade enables the production of low pressures, which enables efficient separation of the cyclic diester from the polymer melt. It is hereby particularly advantageous that the cascade of at least 2 ejector pumps is designed without intermediate condensation. With respect to such a cascade with intermediate condensation, reference is made to US 2009/0299018 which indicates a corresponding cascade, in particular in FIG. 2 and also associated description. Such a cascade without intermediate condensation is also used in the device according to the invention illustrated in FIG. 1. This cascade is characterised there with the reference numbers 3a, 3b, 3c. The intermediate condensation represents an additional complexity which is generally required for not restricting the power of the jet pumps too greatly or delimiting the propellant consumption. It was found that, in the present case, up to 3 jet pumps can be operated without intermediate condensation, the power and propellant consumption being acceptable.

Preferred demonomerisation devices are thereby selected from the group consisting of falling-film evaporators, falling-strand evaporators, vent extruders, vacuum kneaders, steam separators and/or thin-film evaporators.

Further advantages arise, if subsequent to the at least one device for producing a vacuum, at least one condenser, in particular a surface condenser, is connected, which is in fluidic connection with an outlet of the at least one device for producing a vacuum. This embodiment provides that the process vapours or gases emerging from the at least one device for producing a vacuum are condensed out, the condensable components, such as for example possibly contained cyclic diesters according to general Formula I or the corresponding acids forming the cyclic diester of Formula I can be condensed out and hence removed.

It is possible in addition that, subsequent to the at least one condenser, at least one condensate-collecting container is connected, which is in fluidic connection with the at least one condenser, is connected in particular with pipework.

A further embodiment provides that, in front of the at least one condenser and/or the at least one device for producing a vacuum, at least one device for producing an initial vacuum, in particular at least one water-ring pump, is connected, which is in fluidic connection with the at least one condenser and/or the at least one device for producing a vacuum. Pre-connection of a further device for producing an initial vacuum before the actual devices for producing the vacuum improves the quality and stability of the vacuum. With the device for producing the initial vacuum, in particular a water-ring pump, typically pressures of approx. 40 mbar can be produced. With the actual devices for producing the vacuum, for example the cascade of jet pumps, typically pressures of 1 mbar and less can be produced.

A further preferred embodiment provides that the device according to the invention comprises a purification column which is in particular a stripping column. This purification column can be connected subsequent to the at least one condensate-collecting container, to the at least one device for producing a vacuum and/or to the at least one condenser and is in fluidic communication with the respective previously-mentioned components. The purification column thereby has a top-side inlet for condensate, a base-side gas inlet, a top-side gas outlet and also a base-side liquid outlet. By means of this purification column, soluble volatile components therein, in particular volatile decomposition products of the cyclic diester of general Formula I, such as for example volatile aldehydes, in particular acetaldehyde etc., can be separated from the condensate and withdrawn via the gas outlet.

A further embodiment of the device according to the invention provides that, subsequent to the at least one purification column, in particular to the stripping column, to the at least one device for producing a vacuum, to the at least one condenser and/or to the at least one condensate-collecting container, at least one steam producer is connected, which has a liquid inflow which is in fluidic connection with the at least one purification column, in particular the stripping column, via the liquid outlet, with an outlet of the at least one device for producing a vacuum, with the at least one condenser and/or with the at least one condensate-collecting container. The produced condensate can hence be supplied to the steam producer and be evaporated again. This embodiment is preferred in particular when the device for producing a vacuum is a steam ejector pump. In this respect, the water which is used in vaporous form for driving the steam ejector pump is in a circulation. Hence the requirement for fresh water for operation of the jet pumps is crucially reduced, likewise the occurring waste water which increases the economic efficiency of the jet pump operation.

It is further preferred if the at least one steam producer
 a) comprises at least one burner which has at least one supply line for fuel and also a supply line of gaseous oxidant for the fuel, which is in fluidic connection with the top-side gas outlet of the purification column, in particular of the stripping column; and/or
 b) has a discharge for produced steam, which is connected to a steam ejector pump or to a cascade of at least two, preferably at least three, steam ejector pumps so that the steam ejector pump or the cascade of at least two, preferably at least three, steam ejector pumps can be operated by steam produced by the steam producer.

With such a steam producer, for example the volatile components separated from the polyester melt can be supplied directly to the burner and oxidated or combusted there and hence disposed of. The thereby resulting additional waste heat can be used to produce steam. In the case where the devices for producing the vacuum concern steam ejector pumps, the steam produced by the steam producer can be used directly for operation of these devices.

The invention likewise relates to a method for separating and recovering a cyclic diester of general Formula I,

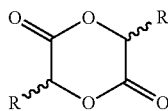

Formula I

R being selected from hydrogen or linear or branched aliphatic radicals with 1 to 6 carbon atoms, from polymer melts comprising the diester of general Formula I, with a device according to the invention in which the polymer melt is supplied with vacuum in at least one demonomerisation device and the diester of general Formula I is separated at least partially or completely from the polymer melt by transition into the gaseous aggregate state and the removed gaseous diester of general Formula I, in at least one separation device by cooling to temperatures below the triple point temperature,
  a) is converted into the solid aggregate state at pressures above the triple point pressure of the diester of Formula I on a surface, temperature-controlled to below the triple point temperature, of the at least one separation device, or
  b) is desublimated at pressures below the triple point pressure of the diester of Formula I on a surface, temperature-controlled to below the triple point temperature, of the at least one separation device.

The invention hence relates to two alternative embodiments. On the one hand, the separation of the diester of Formula I can be effected below the pressure at the triple point of the diester (and simultaneously below the triple point temperature of the diester of Formula I), in this case, a desublimation of the diester of Formula I is effected on the cold parts of the separation device. The diester of Formula I is condensed onto the cooled surfaces of the separation device with a structure similar to hoar frost.

Preferably, the separation is however effected above the pressure at the triple point of the diester of Formula I, however the temperature hereby is below the triple point temperature of Formula I. In this case, firstly a condensation to form fine liquid droplets (mist) is effected, which subsequently solidify on the cold parts of the separation device to form a compact layer.

Discharge of the separated diester from the at least one separation device is effected after melting of the diester.

The method according to the invention surprisingly enables the separation of the diester of Formula I with a high yield and at the same time high purity. In addition, the present method effects simple enrichment of the diester which is obtained in solid form in the separation device. After increasing the pressure in the container above the triple point of the separated diester, the latter can be removed in liquid form from the separation device by melting in a simple manner.

A preferred embodiment of the method provides that the diester of general Formula I is converted into the liquid aggregate state after desublimation or separation in the solid aggregate state and is collected on the base-side in the at least one separation device, and subsequently discharged from the at least one separation device. The obtained diester has high purity and can be transferred for example directly to a polycondensation reaction for producing a polymer from the diester, for example by ring-opening polymerisation. Possibly, the diester can also be transferred into a collection tank after discharge and stored there intermediately.

The means of the at least one separation device for desublimation or conversion into the solid aggregate state of the diester of general Formula I are preferably flowed through alternately with a medium temperature-controlled to below the triple point temperature and for conversion into the liquid aggregate state with a medium temperature-controlled to above the triple point temperature. According to this embodiment, an alternating operation of the separation device is possible so that, during a cycle during which the separation device is flowed through with a cold medium, a separation of the diester under the respective conditions is possible. When passing through the cycle in which the separation device is heated, the diester can be thawed and accumulates on the base of the separation device from where discharge is possible via the outlet.

In addition, it is preferred if, within the at least one separation device during desublimation or conversion into the solid aggregate state of the diester of general Formula I, a pressure which is reduced in comparison to the conversion into the liquid aggregate state is set, the pressure during conversion into the liquid aggregate state being set preferably to at least 2.5 mbar, further preferred from 2.5 to 1,050 mbar, particularly preferred from 10 to 50 mbar.

Melting of the separated diester can also be effected at the same pressure as that during separation. In this case, the pressure is at least 2.4 mbar, preferably 2.5-50, particularly preferred between 2.5 and 10 mbar.

Furthermore, it is preferred if at least two separation devices are included, which are operated alternately. This method implementation allows a quasi-continuous separation of diester from the polymer melt.

In the case where a desublimation of the diester of Formula I is implemented, i.e. the operation takes place at pressures below the triple point pressure, it is necessary that the pressure in the demonomerisation is naturally at least the same, because of the pressure loss in the flow direction, is preferably 0.01 mbar to 1 mbar above the pressure in the separator. In particular, the pressure in the at least one demonomerisation device is set at at most 1.4 mbar, preferably from 0.01 to 1.4 mbar, particularly preferred from 0.1 to 1.4 mbar and also the pressure in the at least one separation device during the desublimation is set at at most 1.4 mbar, preferably from 0.01 to 1.4 mbar, particularly preferred from 0.1 to 1.4 mbar.

On the other hand, a conversion of the diester into the solid aggregate state above the triple point of the diester of Formula I is likewise possible. The pressure hereby in the at least one demonomerisation device is at most 1,050 mbar, preferably from 1.4 to 1,050 mbar, particularly preferred from 1.4 to 100 mbar and also the pressure in the at least one separation device during the conversion into the solid aggregate state is set at at most 1,050 mbar, preferably from 1.4 to 1,050 mbar, particularly preferred from 1.4 to 100 mbar.

The previously mentioned embodiments which denote absolute pressures are thereby advantageous in particular for dilactide as diester of general Formula I, i.e. R=methyl.

Regarded absolutely, the method according to the invention therefore functions in an operating range of 0.01 mbar to 1,050 mbar, preferably 0.1 mbar to 100 mbar, with the proviso that, during the separation process, the cooling elements in the separation device are cooled to temperatures at which solidification of the lactide can be effected.

The steam from the jet pumps is preferably conducted into a condenser. The water vapour which is used for operation of the jet pumps condenses together with the residual quantities of the cyclic diester and decomposition products from the demonomerisation. Residual gas which is not condensable remains, e.g. leakage air from the process. The residual gas is suctioned off by the initial vacuum pump and conveyed into the environment or into the furnace.

The condensate is fed, for further preference, at the top-side into the at least one purification column, preferably into the at least one stripping column and supplied in counterflow with a purification gas, preferably air. This embodiment enables separation of dissolved decomposition products of the PLA from the condensate, such as for example aldehydes, in particular acetaldehyde, which can hence be correspondingly separated and disposed of.

Furthermore, it is advantageous if the condensate which is removed from the at least one purification column, preferably from the at least one stripping column at the base-side, is supplied to the at least one evaporator and evaporated there, the resulting steam being used for operating the steam ejector pump or the cascade of a plurality of steam ejector pumps.

The purification gas which is removed from the top-side gas outlet of the purification column can be fed, together with the oxidant, in particular air or oxygen, for the fuel into the at least one burner of the at least one steam producer.

In particular, the method is suitable for separating lactide or glycolide from polyester melts, in particular polylactide or polyglycolide and/or copolyesters hereof. In the case of lactides or polylactides, any stereoisomer of the lactides can be separated from a corresponding polyester melt.

BRIEF DESCRIPTION OF THE DRAWINGS

The present invention is explained in more detail with reference to the accompanying Figure and also the subsequent embodiments without restricting the invention to the special parameters represented there.

DETAILED DESCRIPTION OF THE INVENTION

Figure 1:
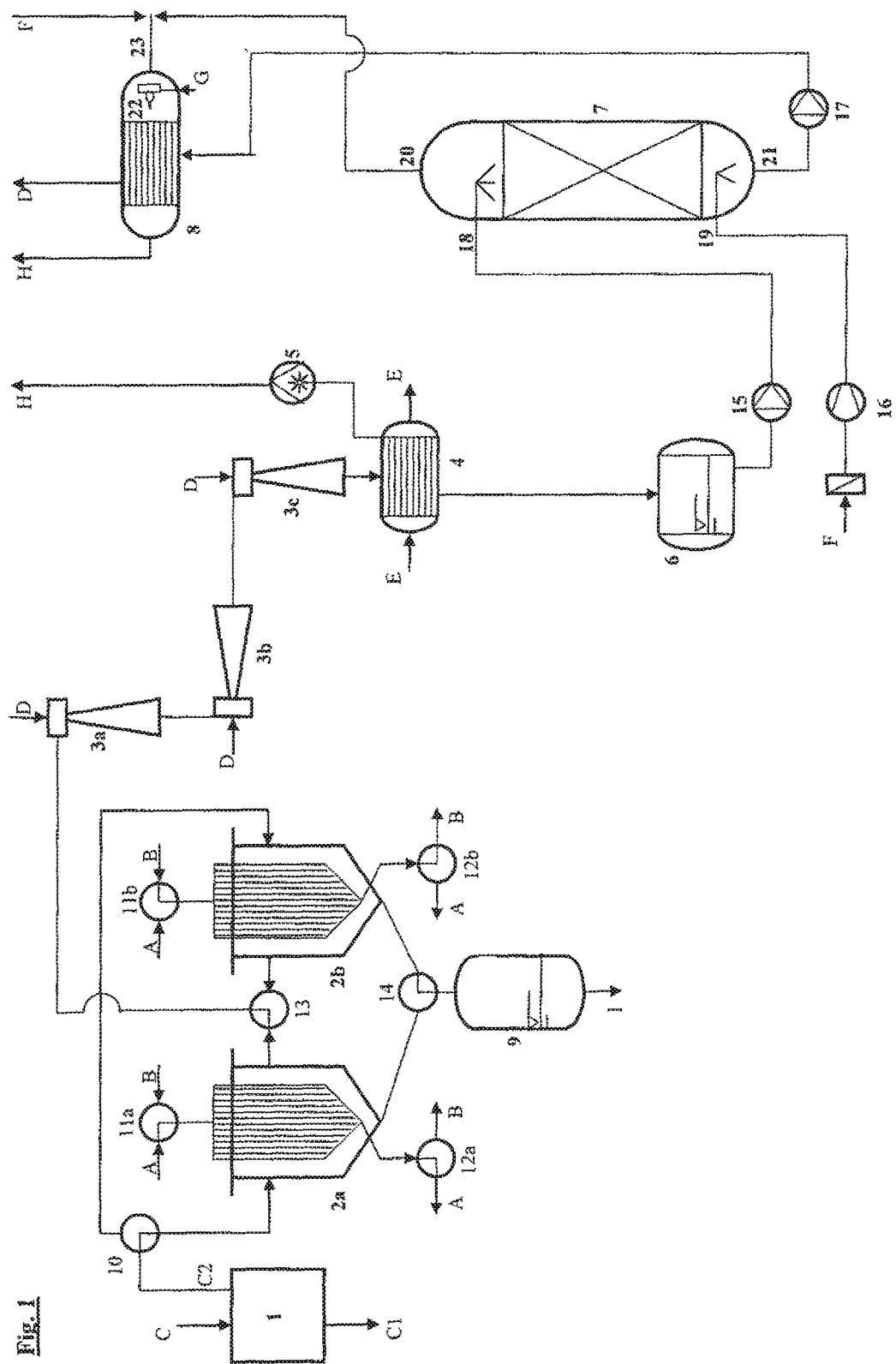
FIG. 1 shows a construction, by way of example, of a device according to the invention for implementing a method according to the invention.

The device according to the invention thereby comprises a demonomerisation device 1 which has a melt inlet C and also a melt outlet C1 for a polyester, for example polylactide. The demonomerisation device 1 has a gas outlet C2 which is connected to a three-way valve 10. Via the three-way valve 10, optionally one separation device 2a or 2b can be provided with a gas flow from the demonomerisation device 1. Each of the separation devices 2a and 2b thereby has an identical construction and has cooled surfaces in the interior. These surfaces can be supplied with a cold medium A or warm medium B via switches 11a or 11b. In FIG. 1, an alternate operation of the two separation devices 2a and 2b is illustrated, the separation device 2a is hereby provided momentarily via the switch 11a with a cold medium A whilst the separation device 2b is supplied with a warm medium B via the switch 11b. After passing through the cooling body, the medium A or B is discharged out of the respective separation device 2a or 2b via a switch 12a or 12b. In the case of FIG. 1, supply of the gas flow C2 originating from the demonomerisation device 1 is effected momentarily into the separation device 2a. Separation of the cyclic diester contained in the gas flow is hereby effected, for example of the lactide on the cooled surfaces of the separation device 2a in the solid state. Both deposition devices 2a and 2b are thereby connected to a cascade of steam ejector pumps 3a, 3b and 3c via a switch 13. As is evident in FIG. 1, merely the separation device 2a is supplied with vacuum momentarily via the switch 13. The separation device 2b, in the state illustrated in FIG. 1, is momentarily in regeneration, the cooled surfaces of the separation device 2b being flowed through with a warm medium B. Any solid cyclic diester, for example lactide, which is already situated on the now heated surfaces is hence heated and, at correspondingly high pressures and high temperatures, is converted into the liquid phase. The liquid diester hence drips down on the heated surfaces and accumulates on the base of the separation device 2b and can be discharged there via an adjustment switch 14 and supplied to a collection container 9. The collection container 9 has a base-side outlet I.

The cascade of steam ejector pumps 3a, 3b, 3c is supplied respectively with steam D. Subsequent to the steam ejector cascade, a condenser 4 is connected, in which steam discharged from the steam ejector pumps and also components not separated in the separation devices 2a or 2b can be condensed. The condenser 4 is thereby operated with a cooling medium E and comprises cooled surfaces, e.g. a pipe bundle, disposed in the interior. Subsequent to the condenser 4, a water-ring pump 5 is connected in order to produce an initial vacuum which can be for example 40 mbar. Corresponding waste gases H can be discharged to the environment without further purification or are combusted in the furnace of the steam producer D.

In addition, FIG. 1 describes an embodiment in which, subsequent to the condenser, a collection tank 6 is connected, in which corresponding aqueous condensates can be collected and stored. The collection tank 6 is connected via a pump 15 to a stripping column 7 which has a top-side supply line 18 for the condensate. The supply line can have for example a trickle head or spray nozzle so that the condensate is distributed uniformly over the column cross-section. In addition, the stripping column has a gas inlet 19 which is disposed in the vicinity of the base and with which a gas F, for example air, can be blown into the stripping column 7 via a fan 16. Hence, air is directed in counterflow to the condensate which is trickled in at the top, as a result of which the condensate can be freed of volatile components. These can be discharged out of the stripping column 7 via the top-side gas outlet 20, whilst the purified condensate collects on the base and can be discharged there out of the stripping column 7 at the base-side 21. Via a pump 17, supply of the condensate to a steam producer 8 is possible, in which steam D is produced from the condensate and can be used again for operation of the cascade of steam ejector pumps 3a, 3b, 3c. The gases discharged at the top-side 20 from the stripping column 7 can be fed into the supply for oxidant 23 of a gas burner 22 which is operated with a fuel G. Hence, volatile components which have been separated from the condensate in the stripping column 7 can be combusted. The waste air H of the steam producer 8 is discharged into the environment.

In the following, a preferred embodiment, given by way of example, for implementing a method according to the invention is indicated, which method illustrates the invention with reference to the example of separation of lactide from a lactide-comprising polylactide (PLA) melt.

A monomer-containing PLA melt is freed of lactide after polymerisation in the known manner by evaporation in the vacuum. This can take place continuously or discontinuously. The examples are static methods, such as free flowing off of the PLA melt in the vacuum over surfaces of baffles, such as inclined metal sheets, static mixers or material exchange packings or free-falling melt films, -strands or -threads in vacuum chambers, mechanically forced movement of the melt, such as in a vent extruder, a vacuum kneader or distribution in a thin layer over heated surfaces with the help of mechanical wipers (thin-film evaporators). It is common to all these methods that they assist evaporation by vacuum and/or carrier gas, large surfaces, heat supply and mixing and thus produce a lactide-containing vapour flow.

In the method according to the invention, the firstly vaporous lactide is separated in solid form after guiding out of the device for demonomerisation by cooling in the vacuum. Demonomerisation and separation of the lactide are effected for instance at the same pressure, a small pressure gradient from the demonomerisation to the separation being maintained by arranging the vacuum system after the separation in order to effect transport by flow in this direction. Cooling of the vapours is effected on cooled surfaces. The cooled surfaces are disposed in a container under vacuum which is termed here lactide separator.

The admixing of cold inert gas to the lactide vapour flow for cooling purposes is avoided because the non-condensable gas flow which is ultimately to be compressed from the vacuum to ambient pressure thereby becomes too high and thereby consumes a lot of energy. Without the addition of inert gas, the lactide is easier to separate from the gas phase and to obtain in compact form (not as powder).

The separation can take place at pressures below the pressure at the triple point of the lactide, i.e. thus by desublimation. The separation of the lactide by desublimation produces a particularly pure lactide since it occurs directly in crystalline form which extensively excludes impurities. This lactide can be returned directly to the polymerisation process or after hydrolysis to the polycondensation because of its purity. The above-mentioned accompanying substances which would lead to discolouration or ring-opening of the lactide can be maintained at a particularly low concentration level. The lower separation temperature during desublimation, compared with the condensation, reduces the danger of ring-opening of the lactide by the last residues of these accompanying substances, such as lactic acid or the linear dimer thereof. Separation on the cooled surfaces as a loose, hoar frost-like layer with partially reduced adhesion is disadvantageous.

However the method functions also at pressures above the pressure at the triple point, the separation temperature requiring to be below the lactide melting point. This separation temperature should be sought and set below the temperature at the triple point of the pure L lactide and depends upon the mentioned impurities in the lactide. These displace the melting point towards lower values. When cooling the vapour on the cooled surfaces, the lactide firstly condenses in liquid form as droplets (mist) which form solid layers after impinging on the cooled surfaces of the lactide separator.

This type of separation has the advantage that the droplets adhere well to the cooled surfaces and form compact layers. Removal from the solid surface and entrainment of lactide as a result of the flow of non-separated gases and vapours does not occur here, in contrast to the hoar frost-like layers which are obtained during separation below the pressure at the triple point. As a result, less entrained lactic powder reaches the subsequent vacuum unit, the lactide losses are less and likewise the corrosive and abrasive loading of the vacuum pumps.

Both during the separation above the pressure at the triple point and below it, it must be ensured that the temperature on the cooled surfaces is below the melting temperature of the lactide.

Irrespective of whether the separation pressure is above or below the pressure at the triple point, the choice of separation temperature offers a certain optimisation potential: the lower this temperature is chosen, e.g. by using cold water or liquid cooling means, the more complete is the separation of the lactide from the gas phase. At the same time, the concentration of by-products in the separated lactide also rises however because the condensation- or desublimation temperature thereof is fallen below. It is therefore necessary to find a separation temperature which makes possible high purity of the lactide with tolerable lactide losses in the waste gas of the lactide separator.

The removal of the separated lactide from the separator is preferably effected by periodic increase in the pressure in the container and in the temperature of the pipes and plates coated with lactide above the temperature at the triple point of the lactide. This leads to melting of the solid lactide from the coated surfaces. The liquid lactide thereby collects in the container base. With the help of liquid pumps which are known per se, it is conveyed out of the vacuum to ambient pressure and stored intermediately. The technical design is described in more detail further on in the example.

In the case where the pressure during separation has been already above the pressure at the triple point, an increase in pressure for the melting is in principle unnecessary. However it is recommended both in this case and also during the lactide separation below the pressure at the triple point to increase the pressure during melting until the temperature window between melting point and boiling point of the lactide is sufficiently wide in order to prevent unintentional re-evaporation because of technically unavoidable variations in the temperature control in the container.

Preferably, jet pumps are used for the vacuum production. They do not comprise any movable parts and are therefore particularly robust relative to lactide deposits in solid or liquid form. They can be manufactured without difficulty from corrosion-resistant material. They have also proved to be resistant against abrasion by lactide aerosols. This could not be expected by the person skilled in the art since the flow velocity of the vapour in these pumps reaches supersonic speed as is known and solid particles are particularly abrasive at high speeds. Jet pumps are suitable therefore in a particular fashion, in combination with the described lactide separators, for removing lactide from PLA melt. By successive connection of a plurality of jet pumps, pressures below the triple point and thus particularly low residual concentrations in the PLA can be achieved in a simple manner.

The vacuum production with steam jet pumps requires steam as propellant. In order to keep down the fresh water consumption of the plant and the release of waste water to the environment, it is advantageous to recover the water after the jet pumps as completely as possible and to use it again for the steam production. It was found that such circulation control of the water encounters problems. After a short time, the steam jet pumps were no longer thereby able to keep the provided vacuum stable or even to reach it. In order to make the use of jet pumps possible, the cause of the problem and suitable measures to remedy it had to be found.

Surprisingly, it was however found that, despite a water-ring pump which was connected in front of the set of jet pumps on the atmosphere-side, said water-ring pump ensuring the required initial vacuum and removing also volatile by-products together with the residual gas from the water circulation, obviously still dissolved by-products remain in the water and move into the steam producer. As a result, the steam quality is impaired rapidly with a closed water circulation and leads to the mentioned vacuum problems. These are solved by the advantageous arrangement of a stripping column in front of the steam producer. This column withdraws volatile by-products of the PLA polymerisation, which are however soluble in water and hence capable of enrichment, from the water with the help of an air flow. Water and air are guided in counterflow in the stripping column so that the waste air laden with by-products escapes at the upper end of the column. At the lower end, the purified water accumulates and is supplied to the steam producer. This process makes no demands on the quality of the air which is used so that dust-free filtered ambient air can be used.

The waste air of the column can be supplied subsequently to the combustion air for a boiler firing system which is required in any case in polymerisation plants. In this way, the by-products are eliminated in an innocuous and economical way. This is advantageous from an environmental point of view since some of the decomposition products are very malodorous.

Figure 2:
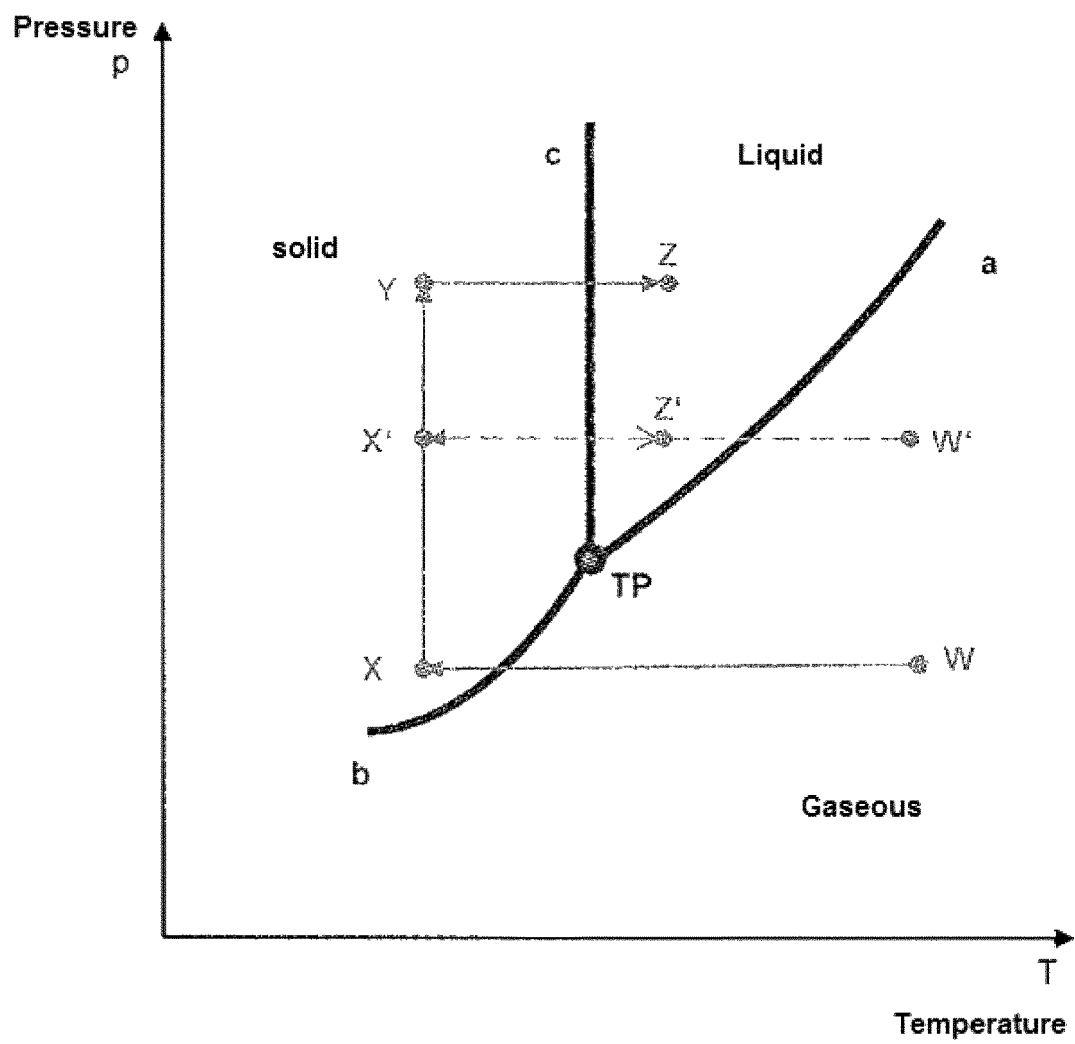
FIG. 2 shows a non-substance-specific phase diagram of a diester used according to the invention.

FIG. 2 shows a phase diagram of a pure substance which here is the diester. P and T are pressure and temperature of the diester in a closed vessel. The drawn curves (a, b, c) separate 3 areas from each other—the solid, liquid and gaseous phase (vapour). The curves meet at the so-called triple point at which all 3 phases are in equilibrium with each other. The triple point is characteristic of the considered pure substance.

"a" is the vapour pressure curve, boiling liquid is in equilibrium with vapour thereon. "b" is the sublimation pressure curve on which solid sublimate is in equilibrium with vapour. "c" is the melting pressure curve, it shows the melting temperature of the diester as a function of the pressure. As with most substances, this dependency is only weakly pronounced and, at the pressures at which the operation takes place according to the invention, is negligible.

A pressure- and temperature scale is absent on the axes of FIG. 2 since the procedure according to the invention is only intended to be explained here in principle. In particular, the value of the triple point and the course of the equilibrium curves depend upon the type of diester. In the case of lactide, also the composition of D, L and mesolactide has an influence on the precise position.

Point W characterises pressure and temperature of the diester vapour which comes from the demonomerisation 1 of FIG. 1, at the entrance of the separator 2a.

The cooled surfaces in the separator have a temperature which is characterised by point X. Point X is, with respect to pressure and temperature, below the triple point of the diester. As a result of cooling on the surfaces, the vapour temperature drops and reaches the sublimation pressure curve "b". There, solid diester is deposited on the cooled surfaces which, after a certain time depending upon the layer thickness, adopts the temperature of the surface (point X). This procedure continues until the available surfaces in the depositor 2a are covered with such thick layers that the heat transfer of the vapour to the surfaces reduces greatly. Consequently, the vapour temperature at the outlet increases, the vapour supply in the separator 2a is ended and the vapour from the demonomerisation is conducted into separator 2b.

For regeneration of separator 2a, the pressure in the container is increased, e.g. by introducing inert gas until point Y is reached. At point Y, the separated diester is at a temperature below the triple point temperature and at a pressure above the triple point pressure. Now the supply of cooling medium A is interrupted and switched over to the heating medium B. The solid diester which adheres to the surfaces is heated, melts, flows away from the surfaces and accumulates in liquid form on the base of the separator. When flowing away from the now heated surfaces, the diester increases the temperature of these surfaces, which is characterised by point Z.

After the melted diester in container 9 has been drained off, the depositor 2a is evacuated again to the pressure prevailing in the container 2b at W and cooled to the temperature at point X. It is thereafter available again for loading as soon as the separator 2b is full.

The path from point W to point X illustrates the separation of the diester below the pressure at the triple point.

The device and the method according to the invention also allow separation of the diester above the pressure at the triple point. The path from point W' to X' in FIG. 2 shows this mode of operation.

Point W' characterises pressure and temperature of the diester vapour coming from the demonomerisation at the entrance of the separator 2a. The cooled surfaces in the separator have a temperature which is characterised by point X'. Point X' is, with respect to the pressure, above the triple point, however below it with respect to the temperature.

As a result of cooling on the cooled surfaces in the separator, the vapour temperature drops with a constant pressure and firstly reaches the region of the liquid phase. The diester condenses out in the form of fine droplets which are separated on the cold surfaces and freeze there due to further dropping of the temperature thereof. A solid layer of diester is formed on the cooled surfaces which, in a certain time which depends upon the layer thickness, adopts the temperature of these surfaces (point X').

The thickness of this layer increases constantly as long as vapour from the demonomerisation 1 is supplied to the separator 2a. If the heat transfer is impeded too greatly by the layer thickness, the temperature at the vapour outlet increases. The vapour supply from the demonomerisation is interrupted and the vapour is conducted into the second separator 2b.

For regeneration, the pressure in the separator 2a is increased at a constant temperature, e.g. by introducing inert gas, until point Y is reached. The further procedure corresponds to the regeneration as described for the separation of the diester below the pressure at the triple point.

In principle, the regeneration after the separation of the diester above the pressure at the triple point is possible also without a pressure increase. The separated diester, the temperature of which is characterised by X', is thereby melted at a constant pressure by temperature increase to a value which is characterised by Z'. After withdrawal of the liquid diester in container 9, the separator is available for a new cycle.

As can be deduced from FIG. 2, the temperature span in which the diester is present as a liquid is significantly smaller than at increased pressure. As a result, the danger increases of again evaporating the diester with imprecise temperature- or pressure control or freezing it and thus not attaining the object of the method.

As an alternative to the method according to the invention, above the pressure at the triple point also a condenser can be used, which should be operated continuously and hence more simply. Below the pressure at the triple point, this alternative is not available and the method according to the invention is the only one possible. For a condenser, the above-mentioned restriction applies however that, in the vicinity above the triple point, the temperature span between solid phase and vapour phase is very small so that, with inadequate control of the temperature or of the pressure, either freezing of the condenser or non-appearance of the condensation occurs. In the vicinity above the triple point, no reliable (disturbance-free) operation of a condenser is therefore possible and the method according to the invention is more advantageous despite the discontinuous operation.

Example 1

This example illustrates the method, the lactide separation taking place below the pressure at the triple point.

In a plant for PLA production by ring-opening polymerisation, the waste gas system of the demonomerisation is executed according to FIG. 1. The waste gas connection pipe of the apparatus for demonomerisation 1 is connected to two lactide separators 2a, 2b, connected in parallel, of which respectively one is in operation and the other is in regeneration. The exit of the lactide separator 2a which is in operation is connected to a set of 3 steam ejector pumps 3a, 3b, 3c which are connected in succession. A water-ring pump 5 which compresses the residual gas flow to ambient pressure produces the initial vacuum for this set.

The lactide separators 2a, 2b are vacuum-tight containers which comprise cooled pipes and plates. Pipes and plates fill the interior which is under vacuum so that the through-flowing hot vapour and gases which are still at 190° C. at the entrance come in intensive contact with the cooled surfaces without short circuit flows occurring. On the outside of the pipes and plates cooled to 40° C. with water from the inside, dilactide in solid form is condensed and forms layers, the thickness of which grows constantly in the course of the operation. The growing layer reduces the heat transfer from the gas to the cooled surfaces so that the separation performance of the apparatus in the course of a cycle becomes less. Before noteworthy quantities of non-separated lactide appear in the gas outlet of the lactide separator, recognisable at this point by a temperature increase, the lactide-containing gas flow from the demonomeriser is switched to the second lactide separator which has been regenerated in the interim and is ready. In the first lactide separator, the vacuum is filled up to 20 mbar by introducing nitrogen so that the pressure is above the triple point. The supply of cooling water is replaced by that of hot pressure water B at 120° C. The lactide layers thereby melt away from the surfaces, liquid lactide accumulates on the base of the lactide separator and is drained off into a heated supply storage tank. From there, it is supplied again for polymerisation. Towards the end of the melting process, the apparatus is again placed under total vacuum and is available for a further desublimation cycle.

The residual gas coming out of the lactide separator which consists of leakage air and the volatile decomposition products of the PLA is suctioned off by 3 jet pumps 3a-3c which are connected in series and operate with steam of 3 bar abs. as propellant. The pump set is operated such that a pressure of 0.5 mbar abs. is applied at the gas outlet of the lactide separator 2a. At the gas outlet of the demonomeriser 1, the pressure is 1.5 mbar as a result of losses in the lactide separator. The steam from the jet pump set is supplied without intermediate condensation to a surface condenser 4, after the $3^{rd}$ step, which is maintained at 24° C. with cold water. The pressure here is 30 mbar. A water-ring pump 5 compresses the residual gas remaining after the condensation to ambient pressure and conveys it to the atmosphere.

The water condensed at the pressure level of 30 mbar flows into a collection container 6 which is at atmospheric pressure because of a height difference of >10 m. From there, it is pumped to the head of a stripping column 7 where it flows in counterflow to air suctioned in from the environment via a filling body packing. At the lower end of the column, the water is purified until it can be supplied to the steam boiler 8 which produces the propellant stream. The waste air from the stripping column 7 is introduced into the supply air of the boiler firing system and combusted.

The lactide accumulating in the lactide separators has, after melting and draining off from the collection container 9, a carboxyl group concentration of 20 mmol/kg and forms a clear colourless melt. Without further purification, it is added to the fresh lactide which serves as raw material for the ring-opening polymerisation in the plant. Recirculation does not change the colour of the amorphous PLA granulate and the average molar mass, measured via the intrinsic viscosity relative to the operation of the plant without this recirculation.

The PLA melt entering into the demonomerisation after the ring-opening polymerisation has a lactide concentration of 4.5%. This concentration C1 in the PLA coming out of the demonomerisation 1 has reduced to a lactide concentration of 0.15%, measured with gas chromatography, after cooling of the melt in water and granulation. In a water sample from container 6, the acid content is measured by titration (analytical method 1) and converted into lactide. This lactide concentration is a measure of the lactide loss by entrainment from the separators 2a and 2b into the vacuum unit. The lactide concentration in the water is 1.5% by weight.

Example 2

This example illustrates the lactide separation above the pressure at the triple point. It corresponds to example 1 with the following differences:

On the outside of the pipes and plates cooled to 35° C. with water from the inside, dilactide is condensed in solid form. The set of vacuum pumps is operated such that a pressure of 4 mbar abs. is present at the gas outlet of the lactide separator 2a. At the gas outlet of the demonomeriser 1, the pressure is 5 mbar as a result of losses in the lactide separator.

The lactide accumulating in the lactide separators has, after melting and draining off from the collection container 9, a carboxyl group concentration of 50 mmol/kg and forms a clear, slightly yellowish melt. Without further purification, it is added to the fresh lactide which serves as raw material for the ring-opening polymerisation in the plant. The recirculation does not change the colour of the amorphous PLA granulate and the average molar mass, measured via the intrinsic viscosity relative to the operation of the plant without this recirculation.

The PLA melt entering into the demonomerisation after the ring-opening polymerisation has a lactide concentration of 4.5%. This concentration C1 in the PLA coming from the demonomerisation 1 has reduced to a lactide concentration of 0.32% (FIG. 1), measured with gas chromatography after cooling of the melt in water and granulation. The lactide concentration in the water from container 6, measured as in example 1, is 0.5% by weight.

Analytical Methods:

1. Carboxyl Groups in the Lactide:

The lactide sample is dissolved in methanol. Subsequently, the solution is titrated with 0.1 N benzylalcoholic KOH solution. The end point is determined potentiometrically.

2. Residual Lactide Content in the PLA:

The PLA sample is dissolved in chloroform and precipitated with isopropanol. The precipitated PLA is filtered off, the low-molecular components thereby remain in the solution. After addition of pentamethylbenzene as internal standard, the solution is separated into its components and detected in the gas chromatograph on a capillary column DB-5; 15/0.32.

3. Determination of the Intrinsic Solution Viscosity:

The weighed-out polymer quantity is dissolved in a defined volume of chloroform. In an Ubbelohde capillary viscometer which is situated in a thermostatic water bath set at 20°+/−0.1° C., the passage time of the solution and of the pure solvent is measured. The quotient of both is the relative solution viscosity. It is converted with the one-point method according to J. Dorgan et al., J. Polym. Sci.: Part B: Polym. Physics, Vol. 43, 3100-3111 (2005) into the intrinsic viscosity (I.V.). The I.V. is in relation to the weight average of the molar mass of the polymer which is described with the so-called Mark-Houwink equation. For the substance pair PLA/chloroform, the equation is (J. Dorgan, loc. sit.):

$$\text{I.V.} = K^* M_w^a, \text{ with } K = 1.53^*10^{-4}, a = 0.759$$

| Legend relating to FIG. 2 | |
|---|---|
| TP | Triple point |
| a | Vapour pressure curve |
| b | Sublimation pressure curve |
| c | Melt pressure curve |
| W → X | Separation below the pressure at the triple point (desublimation) |
| W' → X' | Separation above the pressure at the triple point |
| X/X' → Y | Pressure increase after completion of the separation phase |
| Y → Z | Melting of the diester |
| X' → Z' | Melting of the diester without pressure increase |
| Z/Z' → X/X' | Evacuation and cooling after melting and emptying of the separator |

The invention claimed is:

1. A device for separating and recovering a cyclic diester of general Formula I

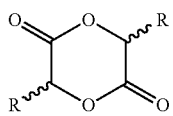

Formula 1

R being selected from hydrogen or linear or branched aliphatic radicals with 1 to 6 carbon atoms, from a polymer melt, comprising the diester of general formula I, which comprises
   a) at least one demonomerisation device for removing the diester of general Formula I in gaseous aggregate state from the polymer melt,
   b) at least one separation device, which is connected subsequent to the at least one demonomerisation device and which is in fluidic connection with the at least one demonomerisation device, for separating the diester of general Formula I, in which the diester of general Formula I is converted via a solid into a liquid aggregate state, and
   c) at least one device for producing a vacuum which is connected subsequent to the at least one separation device and which is in fluidic connection with the at least one separation device,
   wherein, subsequent to the at least one device for producing a vacuum, at least one condenser is connected, which is in fluidic connection with an outlet of the at least one device for producing a vacuum,
   wherein, in front of the at least one device for producing a vacuum, at least one device for producing an initial vacuum is connected, which is in fluidic connection with the at least one condenser and/or the at least one device for producing a vacuum; and
   wherein the at least one device for producing a vacuum is a cascade of at least two ejector pumps, the cascade of at least two ejector pumps being designed without intermediate condensation.

2. The device according to claim 1, wherein the device further comprises at least two separation devices which are operated alternately and are in fluidic connection via a three-way valve with the demonomerisation device and via a three-way valve with the at least one device for producing a vacuum.

3. The device according to claim 1, wherein the at least one separation device has at least one base-side outlet, subsequent to which at least one collection tank for the diester of general Formula I is connected.

4. The device according to claim 1, wherein, subsequent to the at least one condenser, at least one condensate-collecting container is connected, which is in fluidic connection with the at least one condenser.

5. The device according to claim 4, wherein, subsequent to the at least one condensate-collecting container, to the at least one device for producing a vacuum and/or to the at least one condenser at least one purification column, is connected, which is in fluidic connection with the at least one condensate-collecting container, with the at least one condenser and/or with an outlet of the at least one device for producing a vacuum, and has a top-side inlet for condensate and/or vapours, a base-side gas inlet, a top-side gas outlet and a base-side liquid outlet.

6. The device according to claim 5, wherein, subsequent to the at least one purification column, to the at least one device for producing a vacuum, to the at least one condenser and/or to the at least one condensate-collecting container, at least one steam producer is connected, which has a liquid inflow which is in fluidic connection with the at least one purification column, via the liquid outlet, with an outlet of the at least one device for producing a vacuum, with the at least one condenser and/or with the at least one condensate-collecting container.

7. The device according to claim 6, wherein the at least one steam producer
   a) comprises at least one burner which has at least one supply line for fuel and also a supply line of gaseous oxidant for the fuel, which is in fluidic connection with the top-side gas outlet of the purification column; and/or
   b) has a discharge for produced steam, which is connected to a steam ejector pump or to a cascade of at least two steam ejector pumps so that the steam ejector pump or the cascade of at least two steam ejector pumps can be operated by steam produced by the steam producer.

8. A method for separating and recovering a cyclic diester of general Formula I,

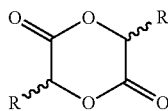

Formula I

R being selected from hydrogen or linear or branched aliphatic radicals with 1 to 6 carbon atoms, from a polymer melt comprising the diester of general Formula I, with a device according to claim 1 in which the polymer melt is supplied with at most 1.05 mbar to the at least one demonomerisation device and the diester of general Formula I is separated at least partially or completely from the polymer melt by transition into the gaseous aggregate state and the removed gaseous diester of general Formula I, in the at least one separation device by cooling to temperatures below the triple point temperature,
a) is converted into the solid aggregate state at pressures above the triple point pressure of the diester of Formula I on a surface, temperature-controlled to below the triple point temperature, of the at least one separation device, the pressure in the at least one demonomerisation device being set at at most 1.050 mbar, and the pressure in the at least one separation device during the conversion into the solid aggregate state being set at at most 1.050 mbar, or
b) is desublimated at pressures below the triple point pressure of the diester of Formula I on a surface, temperature-controlled to below the triple point temperature, of the at least one separation device and hence converted into the solid aggregate state, the pressure in the at least one demonomerisation device being set at at most 1.4 mbar and the pressure in the at least one separation device during the desublimation being set at at most 1.4 mbar, wherein subsequently liquefaction and discharge of the diester of general Formula 1 from the at least separation device is effected.

9. The method according to claim 8, wherein for desublimation or conversion into the solid aggregate state of the diester of general Formula I a medium temperature-controlled to below the triple point temperature and for conversion into the liquid aggregate state a medium temperature-controlled to above the triple point temperature alternatively flow through the at least one separation device, wherein within the at least one separation device during desublimation or conversion into the solid aggregate state of the diester of general Formula I, a pressure which is reduced in comparison to the conversion into the liquid aggregate state is set.

10. The method according to claim 8, wherein at least two separation devices are included, which are operated alternately.

11. The method according to claim 8, wherein steam emerging from the cascade of at least two ejector pumps is condensed in at least one condenser and transferred into at least one condensate-collecting container.

12. The method according to claim 11, wherein the condensed steam is fed, at the top-side, into at least one purification column and supplied in counterflow with a purification gas, wherein
a) the condensed steam which is removed from the at least one purification column at the base-side, is supplied to at least one evaporator and evaporated there, the resulting steam being utilized for operating the cascade of a plurality of ejector pumps, and/or
b) the purification gas which is removed from the top-side gas outlet is fed, together with an oxidant, into at least one burner of at least one steam producer.

13. The method according to claim 8, wherein the polymer melt is a melt of a polyester, and the diester of general Formula I is lactide and/or glycolide.

* * * * *